US00PP19435P2

(12) United States Plant Patent
Valdero

(10) Patent No.: US PP19,435 P2
(45) Date of Patent: Nov. 11, 2008

(54) GRAPE PLANT NAMED 'PINOT GRIGIO/ PINOT GRIS (TEHACHAPI CLONE )'

(50) Latin Name: *Vitis vinifera*
Varietal Denomination: Pinot Grigio/Pinot Gris (Tehachapi Clone)

(75) Inventor: Tom Valdero, Reedley, CA (US)

(73) Assignee: Bronco Wine Co., Ceres, CA (US)

( * ) Notice: Subject to any disclaimer, the term of this patent is extended or adjusted under 35 U.S.C. 154(b) by 0 days.

(21) Appl. No.: 11/800,222

(22) Filed: May 4, 2007

(51) Int. Cl.
*A01H 5/00* (2006.01)

(52) U.S. Cl. ..... Plt./205

(58) Field of Classification Search ..... Plt./205
See application file for complete search history.

*Primary Examiner*—Annette H Para
(74) *Attorney, Agent, or Firm*—Townsend and Townsend and Crew LLP

(57) ABSTRACT

A new distinct variety of grape plant characterized by producing small round white berries suitable for producing outstanding white wine. The new variety distinguishes itself from other white fruit mutations of 'Point Gris' by ripening earlier and having a larger, more prominently winged cluster.

5 Drawing Sheets

Latin name of the genus and species: The grape cultivar of this invention is botanically identified as *Vitis vinifera.*

Variety denomination: The variety denomination is 'Point Grigio/Pinot Gris (Tehachapi Clone)'.

BACKGROUND OF THE INVENTION

The 'Point Noir' grape plant variety is of ancient origin and has been grown in Europe for centuries. It produces outstanding red wine and is one of the most widely planted wine grapes in the world. Numerous mutations of 'Pinot' have been discovered and are economically important varieties in their own right. One of the most important is 'Pinot Grigio/Pinot Gris' (unpatented), which produces reddish-grey colored berries that are used to produce white wine. The red pigments, which can discolor the white wine, must be removed from the wine during fermentation using a process termed "fining." The fining process also removes desirable flavor components, thus reducing wine quality. Wine makers desire to obtain mutations of the 'Pinot' grape plant being completely free of red pigmentation while retaining the characteristic flavor components of the 'Pinot' variety. The 'Pinot Blanc' (unpatented) is such a mutation. It is widely grown and ripens slightly later than the 'Pinot Grigio/Pinot Gris'. Vintners and grape growers also desire mutations that differ in ripening time so that the harvest labor and equipment and vinification facilities are better utilized. An earlier ripening 'Pinot Blanc' type of grape would have great economic value.

BRIEF SUMMARY OF THE INVENTION

The instant variety was discovered as a single cordon mutation of a 'Pinot Grigio/Pinot Gris' plant growing in a commercial vineyard near Arvin, Kern County, Calif. in 2001. One part of the plant produced typical red-gray fruits of the 'Pinot Grigio/Pinot Gris' variety, while the other cordon produced white fruit. Dormant canes from the mutation were grafted onto 'Kober 5C' (unpatented) rootstocks and planted along side 'Pinot Gris' and 'Pinot Blanc' in a test plot in a commercial vineyard near Arvin, Kern County, Calif. The new variety has remained stable and distinct through two generations of asexual propagation using self rooted cuttings and grafting onto '5C' (unpatented) rootstock.

The new grape plant variety 'Pinot Grigio/Pinot Gris (Tehachapi Clone)' is distinguished from its parent variety by producing greenish-white berries compared with the red-gray berries of the 'Pinot Grigio/Pinot Gris' variety.

The grape plant variety 'Pinot Grigio/Pinot Gris (Tehachapi Clone)' may be distinguished from the 'Pinot Blanc' variety, which it most closely resembles, by its earlier ripening and its possessing a cluster with a distinct wing or shoulder as compared with the narrower, more conical cluster of 'Pinot Bland'. On Aug. 5, 2005, 'Pinot Blanc' averaged 21.1 Brix soluble solids, 7.05% titratable acidity, and a pH of 3.47, while the 'Pinot Grigio/Pinot Gris (Tehachapi Clone)' grape plant averaged 21.8 brix, 6.05% acidity and pH 3.45. On Aug. 6, 2006, 'Pinot Blanc' averaged 18.8 brix soluble solids, while the 'Pinot Grigio/Pinot Gris (Tehachapi Clone)' was 19.2 Brix soluble solids. See, Tables 1–2.

TABLE 1

'Pinot Grigio/Pinot Gris (Tehachapi Clone)' vs. 'Pinot Blanc'

| | 'Pinot Blanc' | 'Pinot Grigio/Pinot Gris (Tehachapi Clone)' |
|---|---|---|
| Total berries/cluster | 204 | 223.6 |
| Berries/wing | 1.0 | 62.7 |
| Berry weight | 1.26 g. | 1.4 g. |
| Cluster weight | 255.8 g. | 313.1 g. |

TABLE 2

Soluable solids contents (Brix) of 'Pinot Grigio/Pinot Gris (Tehachapi Clone)' vs. 'Pinot Gris' and 'Pinot Blanc' for 2005 and 2006

| | Jul. 06, 2005 | Jul. 12, 2005 | Jul. 15, 2005 | Jul. 21, 2005 | Aug. 02, 2005 | Jul. 19, 2006 | Jul. 28, 2006 | Aug. 06, 2006 |
|---|---|---|---|---|---|---|---|---|
| Pinot Gris | 12.4 | 16.0 | 18.6 | 21.8 | 25.6 | 13.8 | 16.8 | 20.2 |
| Pinot Blanc | 9.4 | 14.2 | 17.0 | 18.2 | 20.6 | 12.4 | 15.2 | 18.0 |
| Pinot Grigio/ Pinot Gris (Tehachapi Clone)' | 11.6 | 14.6 | 17.2 | 18.8 | 22.0 | 13.4 | 16.2 | 19.2 |

DETAILED DESCRIPTION OF THE INVENTION

Figure 1:
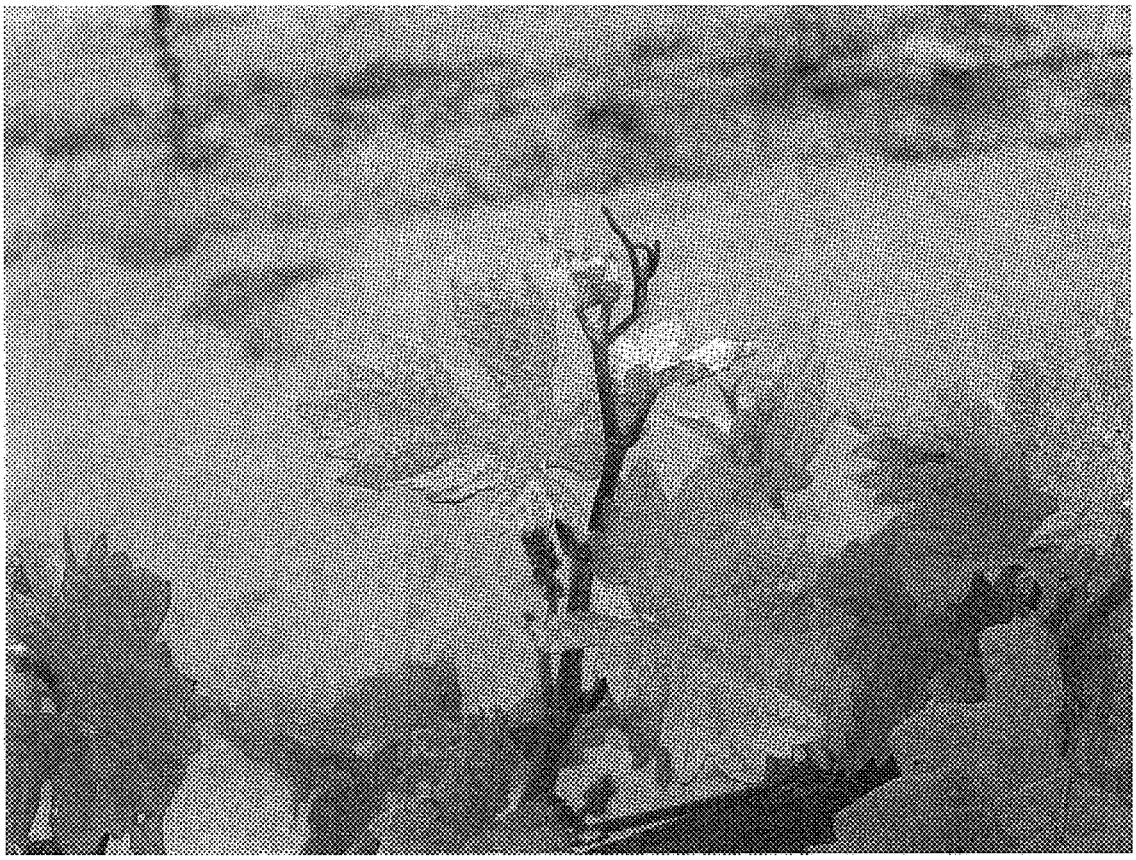
FIG. 1 illustrates a close up photo of the 'Pinot Grigio/Pinot Gris (Tehachapi Clone)' shoot tip.
Figure 2:
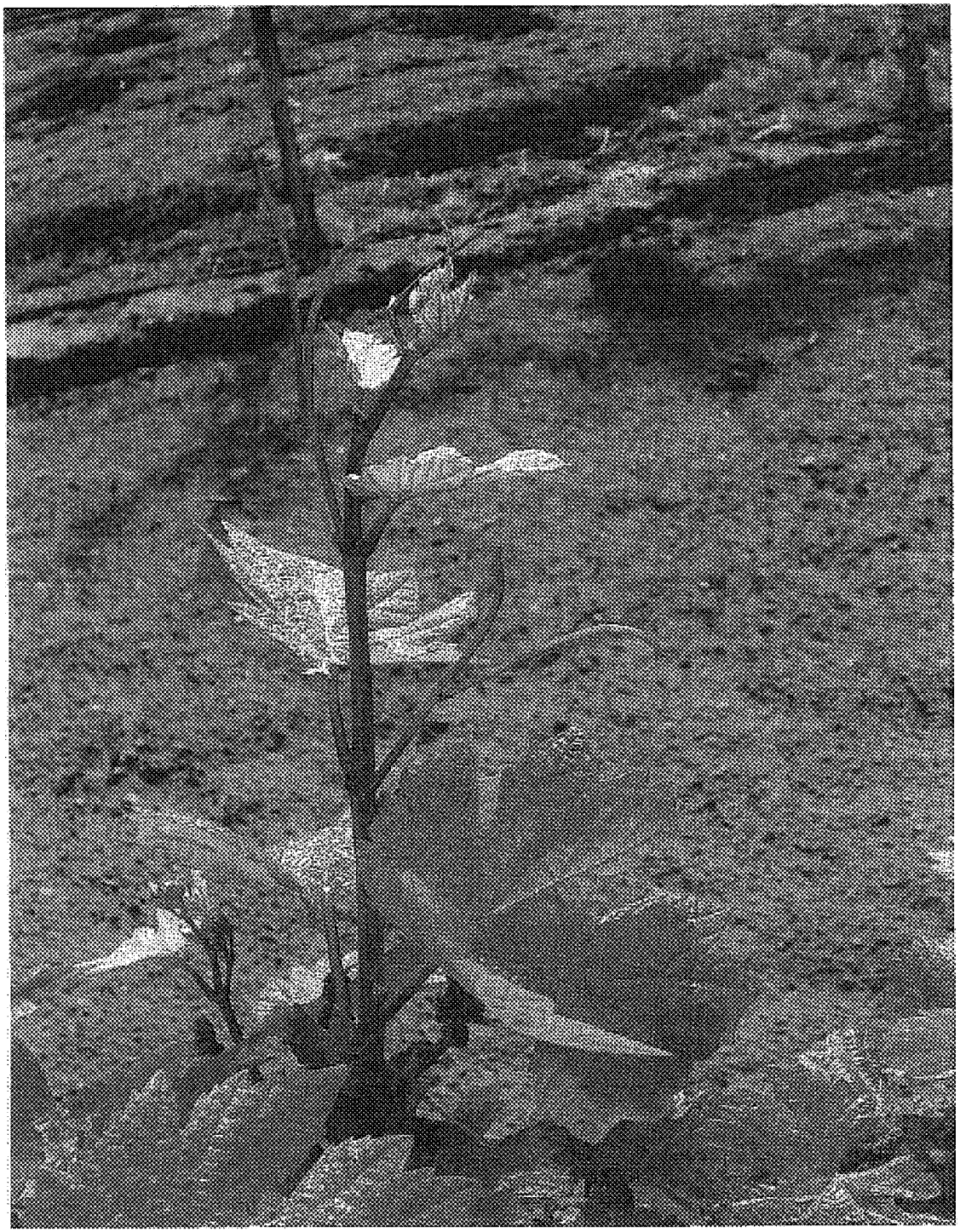
FIG. 2 illustrates a larger view of the 'Pinot Grigio/Pinot Gris (Tehachapi Clone)' vien and shoot tip.
Figure 3:
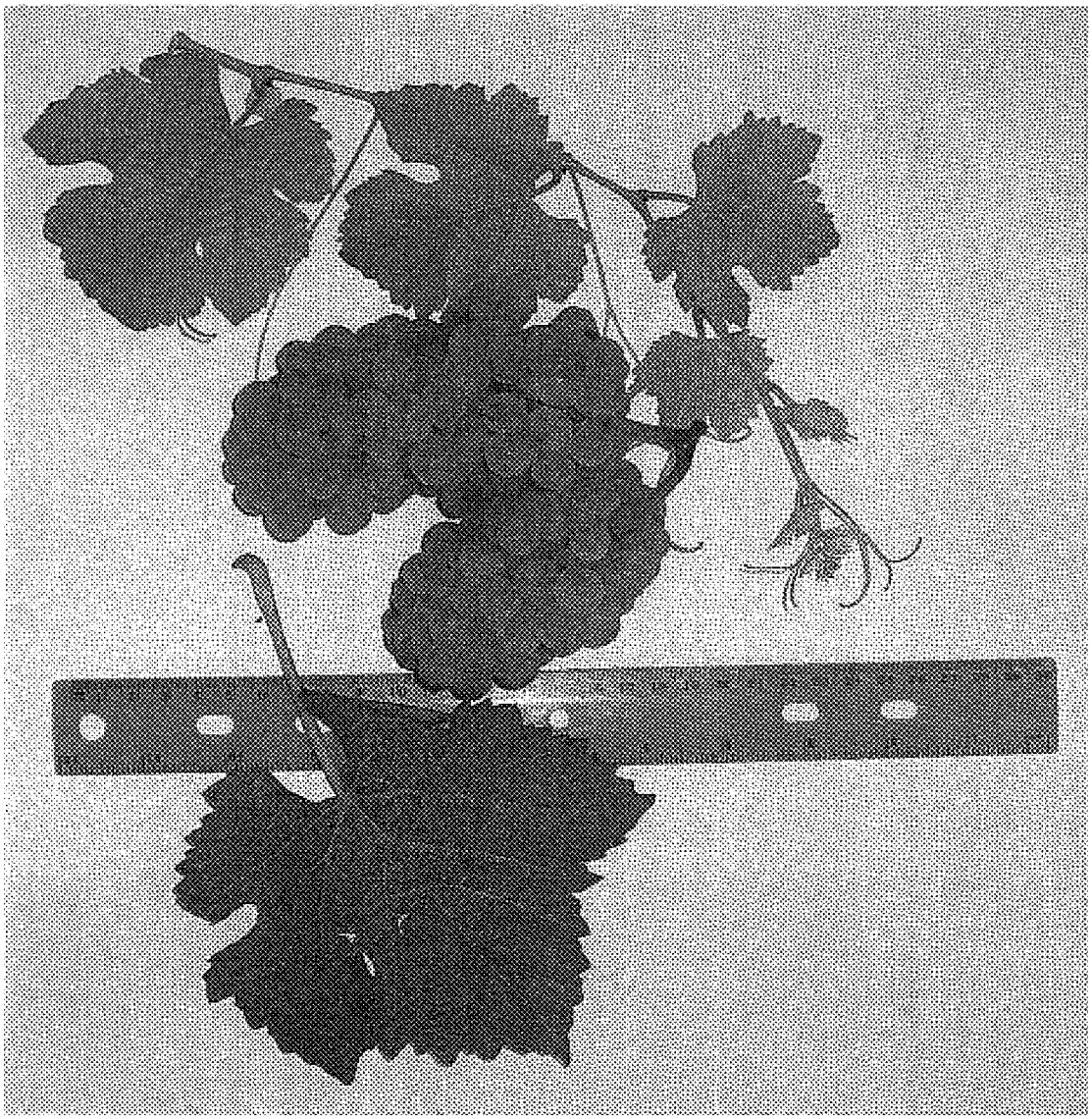
FIG. 3 illustrates a size-scaled photo of the 'Pinot Grigio/Pinot Gris (Tehachapi Clone)' vine and shoot tip, mature berry cluster, and mature leave.
Figure 4:
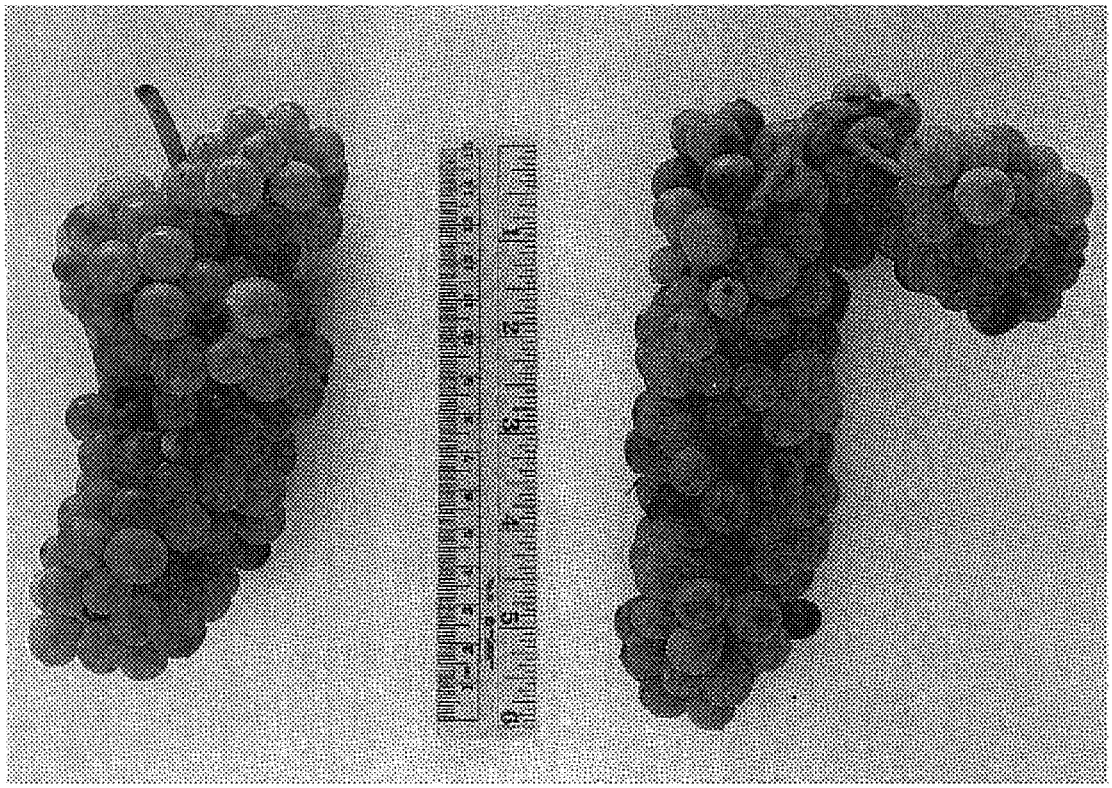
FIG. 4 illustrates a size-scaled photo of the 'Pinot Grigio/Pinot Gris (Tehachapi Clone)' mature berry cluster compared to the 'Pinot Blanc' mature berry cluster.
Figure 5:
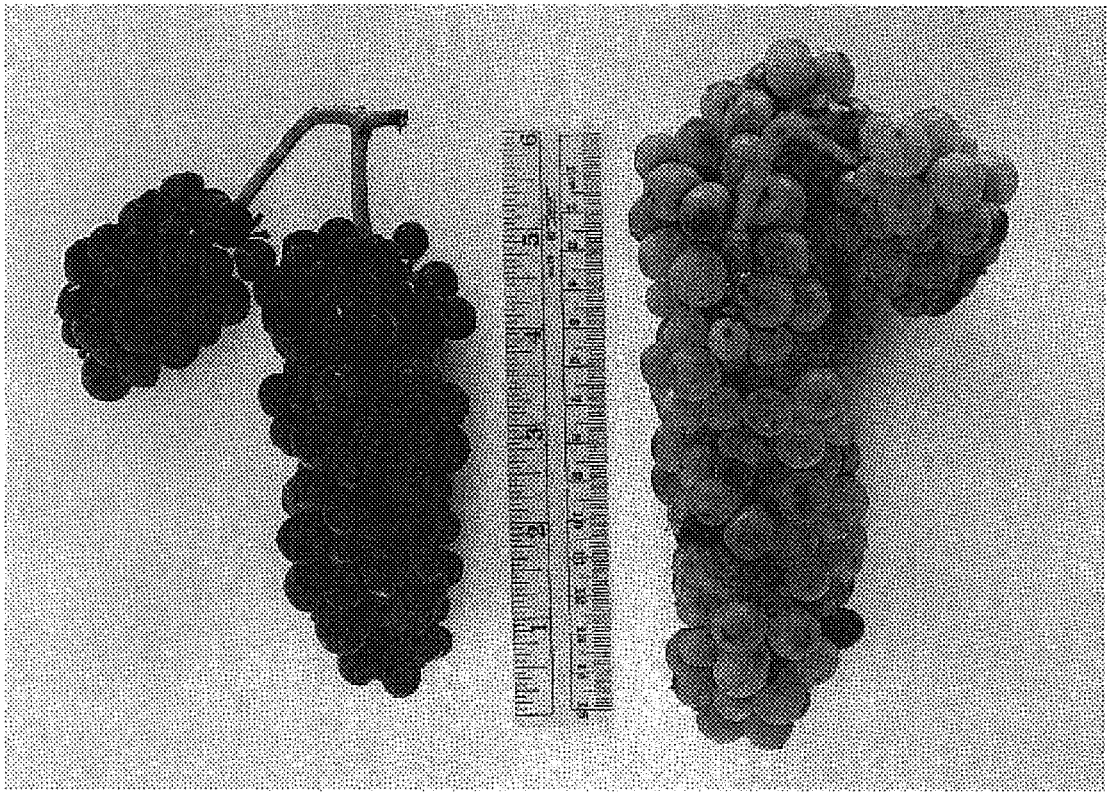
FIG. 5 illustrates a size-scaled photo of the 'Pinot Grigio/Pinot Gris (Tehachapi Clone)' mature berry cluster compared to the 'Pinot Grigio/Pinot Gris' mature berry cluster.

Throughout this specification, color names beginning with a lower case letter signify the name of that color, as used in common speech, is aptly descriptive. Color names beginning with a capital letter designate values based on the R.H.S. Colour Chart, published by The Royal Horticultural Society, London, England.

Many of the description values in this specification are based on and conform to those set forth by the International Board for Plant Genetic Resources Institute Grape Descriptors (*Vitis* spp.) of 1983 and/or 1997 which were developed in collaboration with the Office International de la Vigne et du Vin (OIV) and the international Union for the protection of New Varieties of Plants (UPOV) and published in Descriptors for Grapevine (*Vitis* spp.) (Anonymous, International Plant Genetic Resources Institute, 1997, ISBN 92-9043-352-3).

Vine:

General:

*Vigor.*—Medium.

*Density of foliage.*—Medium.

*Productivity.*—Medium when spur pruned and grown on 5C rootstock.

Trunk:

*General.*—Medium stocky.

*Bark straps.*—Long and split.

*Trunk surface texture.*—Medium shaggy.

*Trunk inner bark color.*—About 177A.

Shoots:

Young shoot:

*Form of tip.*—Fully open.

*Distribution of anthocyanin coloration of the tip.*—Absent.

*Distribution of prostrate hairs of tip.*—Medium to dense.

*Erect hairs.*—Absent from the tip.

Flowering shoot:

*Shoot vigor during flowering.*—Weak.

*Attitude during flowering.*—Horizontal.

*Color of dorsal side of the internodes.*—Green with red stripes.

*Color of ventral side of internodes.*—Green.

*Color of dorsal side of nodes.*—Green with red stripes.

*Color of ventral sides on nodes.*—Green.

*Density of erect hairs on nodes.*—Very sparse.

*Erect hairs on internodes.*—Absent.

*Density of prostrate hairs on nodes.*—Very sparse.

*Density of prostrate hairs on internodes.*—Absent.

*Anthocyanin coloration of buds.*—Weak.

Tendrils:

*Distribution on shoot during flowering.*—Discontinuous.

*Thickness.*—Medium.

*Form.*—Bifuricated to trifurcated.

*Number of consecutive tendrils.*—Up to two.

*Length of tendrils.*—Short, averaging 162 mm.

Leaves:

Young leaves:

*Color of the upper surface of the first four distal unfolded leaves.*—Green.

*Intensity of anthocyanin of six distal leaves prior to flowering.*—Absent or very weak.

*Density of prostrate hairs between veins on the lower surface.*—Sparse to medium.

*Density of prostrate hairs on veins on the lower surface.*—Sparse to medium.

*Density of erect hairs between veins on lower surface.*—Medium.

*Density of erect hairs on veins on lower surface.*—Medium.

Mature leaves:

*Size of blade.*—Medium.

*Shape of blade.*—Wedge shaped.

*Number of lobes.*—3.

*Anthocyanin content of main veins on upper side of leaf.*—Weak.

*Mature leaf profile.*—Involute.

*Blistering of upper surface of blade.*—Strong.

*Leaf blade tip.*—In plane of the leaf.

*Undulation of blade between main and lateral veins.*—Overall.

*Shape of teeth.*—Mixture of both sides straight and both sides convex.

*Length of teeth.*—Short to medium.

*Ratio length/width of teeth.*—Small.

*General shape of petiole sinus.*—Wide open.

*Tooth at petiole sinus.*—Absent.

*Petiole sinus limited by veins.*—Absent.

*Shape of upper lateral sinus.*—Open.

*Depth of upper lateral sinus.*—Medium to deep.

*Density of prostrate hairs between veins on lower surface of blade.*—Sparse.

*Density of erect hairs between veins on lower surface of blade.*—Absent.

*Density of prostrate hairs on veins on lower surface of blade.*—Sparse.

*Density of erect hairs on veins on lower surface of blade.*—Medium.
*Density of prostrate hairs on main veins on upper surface of blade.*—Present.
*Upper surface color.*—About 137A.
*Lower surface color.*—About 137C.
*Fall coloration.*—About 153D.
*Surface texture.*—Rugose.
*Anthocyanin coloration of main veins on lower leaf surface.*—Absent.
*Leaf blade length.*—About 114 mm.
*Leaf blade width.*—About 154 mm.

Petiole:
*Length of petiole.*—Short, about 110 mm.
*Length of petiole compared to middle vein.*—Slightly shorter.
*Density of prostrate hairs on petiole.*—Sparse.
*Density of erect hairs on petiole.*—None.
*Shape of base of petiole sinus.*—V shaped.

Mature canes:

Woody shoot:
*Shape.*—Medium.
*Internode length at first fruiting node.*—Very short, about 46 mm.
*Width at node.*—About 7.4 mm.
*Internode cross section.*—Circular.
*Woody shoot surface.*—Striated.
*Main color.*—Yellowish brown, about 164B.
*Growth of axillary shoots.*—Weak, about 23 cm.
*Lenticels on canes.*—Absent.

Flowers:
*Flower sex.*—Hermaphrodite.
*Length of first inflorescence.*—Very short.
*Position of first flowering node.*—Second.
*Number of inflorescence per shoot.*—2.1 to 3.
*Time of bloom.*—Early.

Fruit:
*Use.*—Wine
*Ripening period.*—Early. .
*Bunch size.*—Small.
*Bunch length.*—Short, about 12.1 cm.
*Bunch width.*—About 11.0 cm.
*Peduncle length.*—Very short, about 3.9 cm.
*Lignification of peduncle.*—Strong.
*Bunch weight.*—256.2 g.
*Berry size.*—Small, about 1.3 g.
*Berry uniformity.*—Uniform.
*Seeds.*—Well developed.
*Cross section.*—Circular.
*Longitudinal axis.*—13.3 mm.
*Horizontal axis.*—12.6 mm.
*Skin color.*—Green-yellow, about 152A.
*Juiciness of flesh.*—Very juicy.
*Berry firmness.*—Very soft.
*Particular flavor.*—None.
*Cuticular wax.*—Medium.
*Pedicel length.*—Short.
*Berry separation from pedicel.*—Medium.
*Visibility of hilum.*—Slightly clear.
*Skin thickness.*—Medium.
*Reticulation.*—Absent.

The above descriptions of the new variety of grape plant pertains to vines growing on '5C' rootstock near Arvin, Kern County, Calif. in the years of 2005 and 2006 (when the plants were five or six years old, respectively) and is believed to apply to plants of the variety grown under similar conditions of culture, solid and climate elsewhere. Variations of the usual magnitude such as differences in maturity dates and production may be due to cultural activities such as irrigation, fertilization, pruning, fruit thinning and climatic changes.

What is claimed is:

1. A new and distinct variety of grape plant having characteristics described and illustrated herein.

* * * * *

'Pinot Blanc'

'Pinot Grigio/Pinot Gris (Tehachapi Cone)'

'Pinot Grigio/Pinot Gris'

'Pinot Grigio/Pinot Gris (Tehachapi Clone)'

UNITED STATES PATENT AND TRADEMARK OFFICE

CERTIFICATE OF CORRECTION

PATENT NO. : PP 19,435 P2
APPLICATION NO. : 11/800222
DATED : November 11, 2008
INVENTOR(S) : Tom Valdero It is certified that error appears in the above-identified patent and that said Letters Patent is hereby corrected as shown below:

In column 2, line 21:

Delete "Bland" and replace it with --Blanc--

Signed and Sealed this

Seventeenth Day of March, 2009

JOHN DOLL
*Acting Director of the United States Patent and Trademark Office*